(12) United States Patent
Wang

(10) Patent No.: US 7,067,308 B1
(45) Date of Patent: Jun. 27, 2006

(54) VECTOR FOR GENETICALLY MODIFYING NON-HUMAN ANIMALS

(75) Inventor: Kangsheng Wang, Rowland Heights, CA (US)

(73) Assignee: Bioagri Corporation, City of Industry, CA (US)

( * ) Notice: Subject to any disclaimer, the term of this patent is extended or adjusted under 35 U.S.C. 154(b) by 0 days.

(21) Appl. No.: 09/537,861

(22) Filed: Mar. 28, 2000

(51) Int. Cl.
*C12N 15/00* (2006.01)
*C12N 15/09* (2006.01)
*C12N 15/63* (2006.01)
*C12N 15/70* (2006.01)
*C12N 15/74* (2006.01)
*C12N 5/00* (2006.01)
*C12N 5/02* (2006.01)
*C12N 15/85* (2006.01)
*C12N 15/87* (2006.01)
*C12P 21/08* (2006.01)
*C07K 16/00* (2006.01)

(52) U.S. Cl. .................... 435/320.1; 435/455; 435/325; 530/388.1; 530/387.1; 800/21; 800/25

(58) Field of Classification Search ................ 435/455, 435/463, 320.1, 325; 800/18, 21, 22, 25, 800/3; 530/388.1, 387.1
See application file for complete search history.

(56) References Cited

U.S. PATENT DOCUMENTS

| 5,428,132 | A | 6/1995 | Hirsch et al. | ............. | 530/387.1 |
| 5,521,291 | A | 5/1996 | Curiel et al. | ............. | 530/391.7 |
| 5,744,335 | A | 4/1998 | Wolff et al. | ............. | 435/172.3 |

FOREIGN PATENT DOCUMENTS

| CN | 1208600 | 2/1999 |
| EP | 0 431 839 A1 | 6/1991 |
| EP | 0 431 839 B1 | 6/1991 |
| RU | 2081914 | 6/1997 |
| WO | WO 90/08192 | 7/1990 |
| WO | WO 93/24626 | 12/1993 |
| WO | WO 97/11597 | 4/1997 |
| WO | WO 99/38991 | 8/1999 |
| WO | WO 99/40213 | 8/1999 |
| WO | WO 99/42569 | 8/1999 |
| WO | WO 00/08924 | 2/2000 |

OTHER PUBLICATIONS

Gandolfi; Spermatoza, DNA binding and transgenic animals, 1998, Transgenic Research 7: 147-155.*
Wolf et. al.; Special Review Series—Gene Manipulation and Integrative Physiology, 2000, Experimental Physiology 85: 615-625.*
Squires; Status of Sperm-mediated Delivery Methods for Gene Transfer, 1999, Transgenic Animals in Agriculture: 87-95.*
Gandolfi; Sperm-Mediated Transgenesis, 1999, Theriogenology 53: 127-137.*
Sperandio et. al.; Sperm-Mediated DNA Transfer In Bovine and Swine Species, 1996, Animal Biotechnology 7(1): 59-77.*
Chang et. al.; Production of Cermline Chimeric Chickens by Transfer of Cultured Primordial Germ Cells, 1997, Cell Biology International vol. 8: 495-499.*
Wallen-Ohman; Ligation of MHC class 1 induces apoptosis in human pre-b cell lines, in promyelocytic cell lines and in CD40-stimulated mature B cells, 1997, International Immunology vol. 9, No. 4: 599-606.*
Sarkar et.al.; Distribution of 105kDa Sperm Unique Antigen on Goat Epididymal Mature Spermatozoa, 1997, Biochemical and Biophysical Research Communications 231: 662-666.*
Yan et al., Characterization of Sperm Agglutinating Monoclonal Antibody and Purification of the Human Sperm Antigen, 1986, Int. J. Fertil. 31: 77-85.*
Nakamura et al. Identification and Characterization of a Sperm Peptide Antigen Recognized by a Monoclonal Antisperm Autoantibody Derived from a Vasectomized Mouse. Biochemical and Biophysical Research Communications. 205: 1503-1509, 1994.*

(Continued)

*Primary Examiner*—Joseph Woitach
*Assistant Examiner*—Thaian N. Ton
(74) *Attorney, Agent, or Firm*—Michael J. Wise; Perkins Coie LLP

(57) ABSTRACT

The present invention is directed to a vector and its use to generate genetically modified animals and cells. One aspect of this invention involves a vector that comprises a sperm cell and one or more polynucleotide molecules bound to a sperm cell through one or more non-liposome based linkers. In a preferred embodiment of this invention, the linker is a protein or polypeptide, preferably sperm specific such as an antibody that binds with the external surface of the sperm cell. In another aspect of the present invention, genetically modified cells or animals are derived from the fertilization of an animal egg cell with the vector described. In one preferred embodiment, genetic modification occurs with the polynucleotide molecule integrating, wholly or partially, into the cell or animal's genome. Another aspect of the present invention includes cells, such as sperm cells or egg cells, and cell lines that are derived from these genetically modified animals or their descendants. In another aspect of the present invention, the genetically modified animals derived from the use of the sperm vector described above possess certain desired characteristics. Examples of these characteristics include faster growth rates, disease or pathogen resistance, high production of certain proteins in milk, and organs suitable for animal to human xenotransplantation.

23 Claims, 16 Drawing Sheets

OTHER PUBLICATIONS

Naz et al. Antibodies to Sperm-Specific Human FA-1 Inhibit in vitro Fertilization in Rhesus Monkeys: Development of a Simian Model for Testing of anti-FA-1 Contraceptive Vaccine. Journal of Repoductive Immunology. 27: 111-121, 1994.*

Kim et al. Effects of Experimentally Generated Bull Antisperm Antibodies on in vitro Fertilization. Biology of Reproduction. 60: 1285-1291, 1999.*

Chang et al., "Effective generation of transgenic pigs and mice by linker based sperm-mediated gene transfer," manuscript submitted to BMC Biotech on Nov. 3, 2001.

Brackett et al., Uptake of Heterologous genome by mammalian spermatozoa and its transfer to ova through fertilization, PNAS (1971) 68:353-357.

Perry, AC. et al., Mammalian Transgenesis by intracytoplasmic sperm injection., Science (1999) 284: 1180-1183.

Carballada R., Regulation of foreign DNA uptake by mouse spermatozoa, Exp Cell Research 2001, 262: 104-113.

Smith, K. (1999) "Sperm Cell Mediated Transgenesis: A Review," *Animal Biotechnology* 10(1&2): 1-13.

Gandolfi, F. (1998) "Spermatozoa, DNA Binding and Transgenic Animals," *Transgenic Research* 7(3): 147-155.

Spadafora, C. (1998) "Sperm Cells and Foreign DNA: a controversial relation," *BioEssays* 20(11): 955-964.

Lavitrano, M., et. al. (1999) "Human Decay Accelerating Factor Transgenic Pigs Obtained by Sperm Mediated Gene Transfer," *Transplantation Proceedings* 31: 972-974.

Liu, X.Y., et. al. (1999) Association of Foreign DNA with Sperm of Gilthead Seabream, *Sparus aurata*, After Sonication, Freezing, and Dimethyl Sulfoxide Treatments, *Marine Biotechnology* 1: 175-183.

Hasebe, M., et. al. (1998) "An Attempt to Produce Transgenic Chicken Mediating Sperm Cells as Vectors," *Journal of Applied Animal Research* 14: 143-150.

Rottmann, O.J., et. al. (1996) "Liposome Mediated Gene-Transfer via Sperm Cells. High Transfer Efficiency and Persistence of Transgenes by Use of Liposomes and Sperm Cells and a Murine Amplification Element," *J. Animal Breed. Genet.* 113: 401-411.

Sperandio, S., et. al. (1996) "Sperm Mediated DNA Transfer in Bovine and Swine Species," *Animal Biotechnology*, 7: 59-77.

Maione, B., et. al., (1998) "Sperm-Mediated Gene Transfer in Mice," *Molecular and Development* 50:406-409.

Maione, B., et. al. (1997) "Activation of Endogenous Nucleases in Mature Sperm Cells upon Interaction with Exogenous DNA," *DNA and Cell Biology* 16(9): 1087-1097.

Birnstiel, M. and Busslinger, M., (1989) "Dangerous Liaisons: Spermatozoa as Natural Vectors for Foreign DNA?," *Cell* 57: 701-702.

Dickson, D. (1989) "Dangerous Liasons in Cell Biology" *Science* 244 1539-1540.

Brinster, R.L., et. al., (1989) "No Simple Solution for Making Transgenic Mice," *Cell* 59:239-241.

Tsai, H.J., et. al., (1997) "Sperm as a carrier to introduce an exogenous DNA fragment into the oocyte of Japanese abalone (Haliotis divorsicolor suportexta)," *Transgenic Research* 6(1): 85-95.

Gagne, M. B., et. al., (1991) "Electroporation of Bovine Spermatozoa to Carry Foreign DNA in Oocytes," *Molecular Reprodcution and Development* 29: 6-15.

Lavitrano, M., et. al., (1989) "Sperm Cells as Vectors for Introducing Foreign DNA into Eggs: Genetic Transformation of Mice," *Cell* 57: 717-723.

Wall, R.J., et. al. (1992) Making Transgenic Livestock, Genetic Engineering on a Large Scale, *Journal of Cellular Biochemistry* 49: 113-120.

Francolini, M., et. al (1993) Evidence for Nuclear Internalization of Exogenous DNA into Mammalian Sperm Cells, *Mol. Reprod. Devel.* 34: 133-139.

Lavitrano, M., et. al. (1992) The Interaction Between Exogenous DNA and Sperm Cells, *Mol. Reprod. Devel.*, 31: 161-169.

Pursel, V. G., et.al. (1989) Genetic Engineering of Livestock, *Science* 244: 1281-1288.

Ward, K., (1991) The Application of Transgenic Techniques for the Improvement of Domestic Animal Productivity, *Current Opinion in Biotechnology* 2: 834-839.

Lonnerdal, B. (1996) Recombinant Human Milk Proteins—An Opportunity and a Challenge, *American Journal of Clinical Nutrition* 63: 622-626.

Cozzi, E., et. al. (1994) Expression of Human Decay Accelerating Factor in Transgenics Pigs, *Transplantation Proceedings.* 26: 1402-1403.

Etherton, T.D., et. al. (1993) Mechanism by which Somatotropin Decreases Adipose Tissue Growth, *American Journal of Clinical Nutrition* 58 (Supp.): 287S-295S.

Brinster, Ralph L. et al., "No Simple Solution for Making Transgenic Mice", *Cell, Cell Press*, Cambridge, MA, vol. 59, pp. 239-241 (1989).

Gandolfi, Fulvio, "Spermatozoa, DNA binding and transgenic animals", *Transgenic Research*, vol. 7, pp. 147-155 (1998).

Maione, Barbara et al., "Sperm-Mediated Gene Transfer in Mice", *Molecular Reproduction and Development*, Wiley-Liss, Inc., New York, NY, vol. 50, pp. 406-409 (1998).

Töpfer-Petersen E. et al., "Spermadhesins: A new protein family. Facts, hypotheses and perspectives", *Andrologia*, vol. 30, No. 4-5, pp. 217-224 (1998).

Töpfer-Petersen E. et al., "Sperm-associated protein candidates for primary zona pellucida-binding molecules: structure-function correlations of boar spermadhesins", *Journal of Reproduction and Fertility Supplement 50*, pp. 55-61 (1996).

Gougoulidis, Tiki et al., "Inhibition of Bovine Sperm-Oocyte Fusion by the Carbohydrate GalNAc", *Molecular Reproduction and Development*, vol. 54, No. 2, pp. 179-185 (1999).

Rivkin, Eugene et al., "Molecular Cloning of Rat Sperm Galactosyl Receptor, a C-Type Lectin With In Vitro Egg Binding Activity", *Molecular Reproduction and Development*, vol. 56, No. 3, pp. 401-411 (2000).

Richardson, Richard T. et al., "Sequence of a Rabbit Sperm Zona Pellucida Binding Protein and Localization during the Acrosome Reaction", *Developmental Biology*, vol. 165, No. 2, pp. 688-701 (1994).

Yamasaki, Noriyuki et al., "Expression of the Rabbit Sperm Protein Sp17 in Cos Cells and Interaction of Recombinant Sp17 With the Rabbit Zona Pellucida", *Molecular Reproduction and Development*, vol. 40, No. 1, pp. 48-55 (1995).

Lacy, H. Marie et al., "Sperm protein 17 is expressed on normal and malignant lymphocytes and promotes heparan sulfate-mediated cell-cell adhesion", *Blood*, vol. 98, No. 7, pp. 2160-2165 (2001).

Miller, David J. et al., "Complementarity between sperm surface $\beta$-1,4-galactosyl-transferase and egg-coat ZP3 mediates sperm-egg binding", *Nature*, vol. 357, No. 6379, pp. 589-593 (1992).
Lu, Qingxian et al., "Sperm from β1,4-galactosyltransferase-null mice are refractory to ZP3-induced acrosome reactions and penetrate the zona pellucida poorly", *Development*, vol. 124, pp. 4121-4131 (1997).
Cheng, Alice et al., "Sperm-Egg Recognition in the Mouse: Characterization of sp56, A Sperm Protein Having Specific Affinity for ZP3", *The Journal of Cell Biology*, vol. 125, No. 4, pp. 867-878 (1994).
Bookbinder, L.H. et al., Tissue- and Species-Specific Express of sp56, a Mouse Sperm Fertilization Protein, *Science*, vol. 269, pp. 86-89 (1995).
Hardy, Daniel M. et al., "A Sperm Membrane Protein That Binds in a Species-specific Manner to the Egg Extracellular Matrix Is Homologous to von Willebrand Factor", *The Journal of Biological Chemistry*, vol. 270, No. 44, pp. 26025-26028 (1995).
Gao, Zeren et al., "Species Diversity in the Structure of Zonadhesin, a Sperm-specific Membrane Protein Containing Multiple Cell Adhesion Molecule-like Domains", *The Journal of Biological Chemistry*, vol. 273, No. 6, pp. 3415-3421 (1998).
Burks, D.J. et al., "Interaction of a Tyrosine Kinase from Human Sperm with the Zona Pellucida at Fertilization", *Science*, vol. 269, pp. 83-86 (1995).
Kalab, Petr et al., "p95, the Major Phosphotyrosine-containing Protein in Mouse Spematozoa, Is a Hexokinase with Unique Properties", *The Journal of Biological Chemistry*, vol. 269, No. 5, pp. 3810-3817 (1994).
Cornwall, Gail A. et al., Inhibition of the Mouse Sperm Surface α-D-Mannosidase Inhibits Sperm-Egg Binding in Vitro, *Biology of Reproduction*, vol. 44, No. 5, pp. 913-921 (1991).
Mori, Kazumasa et al., "Blocking of human fertilization by carbohydrates", *Human Reproduction*, vol. 8, No. 10, pp. 1729-1732 (1993).
Pereira, Ben M.J. et al., "Rat Sperm Surface Mannosidase Is First Expressed on the Plasma Membrane of Testicular Germ Cells", *Biology of Reproduction*, vol. 59, No. 6, pp. 1288-1295 (1998).
Kadam, Arjun L. et al., "Fertilization antigen (FA-1) completely blocks human sperm binding to human zona pellucida: FA-1 antigen may be a sperm receptor for zona pellucida in humans", *Journal of Reproductive Immunology*, vol. 29, No. 1, pp. 19-30 (1995).
Zhu, Xiaolong et al., "Fertilization antigen-1: cDNA cloning, testis-specific expression, and immunocontraceptive effects", *Proceedings of the National Academy of Sciences*, vol. 94, No. 9, pp. 4704-4709 (1997).
Anwer, Khursheed et al., "Targeted Gene Delivery: A Two-Pronged Approach", *Critical Reviews in Therapeutic Drug Carrier Systems*, 17(4), pp. 377-424 (2000).
Uherek, Christoph et al., "DNA-carrier proteins for targeted gene delivery", *Advanced Drug Delivery Reviews*, 44(2-3), pp. 153-166 (2000).
Varga, Csanad M. et al., "Receptor-Mediated Targeting of Gene Delivery Vectors: Insights from Molecular Mechanisms for Improved Vehical Design", *Biotechnology and Bioengineering*, vol, 70, No. 6, pp. 593-605 (2000).
Yan, Yuan Chang et al., "Characterization of cDNA encoding a human sperm membrane protein related to A4 amyloid protein", *Proc. Natl. Acad. Sci.*, vol. 87, pp. 2405-2408 (1990).
Kameda, Kinu et al., "Comparative Studies of the Antigens Recognized by Sperm-Immobilizing Monoclonal Antibodies", *Biology of Reproduction*, vol. 46, pp. 349-357 (1992).
Change, Keejong, et al., "Effective generation of transgenic pigs and mice by linker based sperm-mediated gene transfer", BMC Biotechnology 2002, 2:5, http://www.biomedcentral.com/1472-6750/2/5.
Morawatz, R., Written Opinion, issued on Jun. 27, 2002 by PTO regarding International Application No. PCT/US01/07018, which claims the priority to U.S. Appl. No. 09/537,861.
Shaha, Chandrima et al., "Monoclonal Antibody Against a Human Sperm Protein Recognizes Multiple Epitopes on Rabbit and Human Sperm and Blocks Sperm Function," (1993) *Hybridoma*, vol. 12, pp. 709-718.
PCT International Search Report for PCT/US02/40492, dated Jun. 5, 2003, 4 pages.
Pain, B. et al., "Chicken Enbryonic Stem Cells and Transgenic Strategies." Cells Tissues Organs. 1999, vol. 165, pp. 212-219.

* cited by examiner

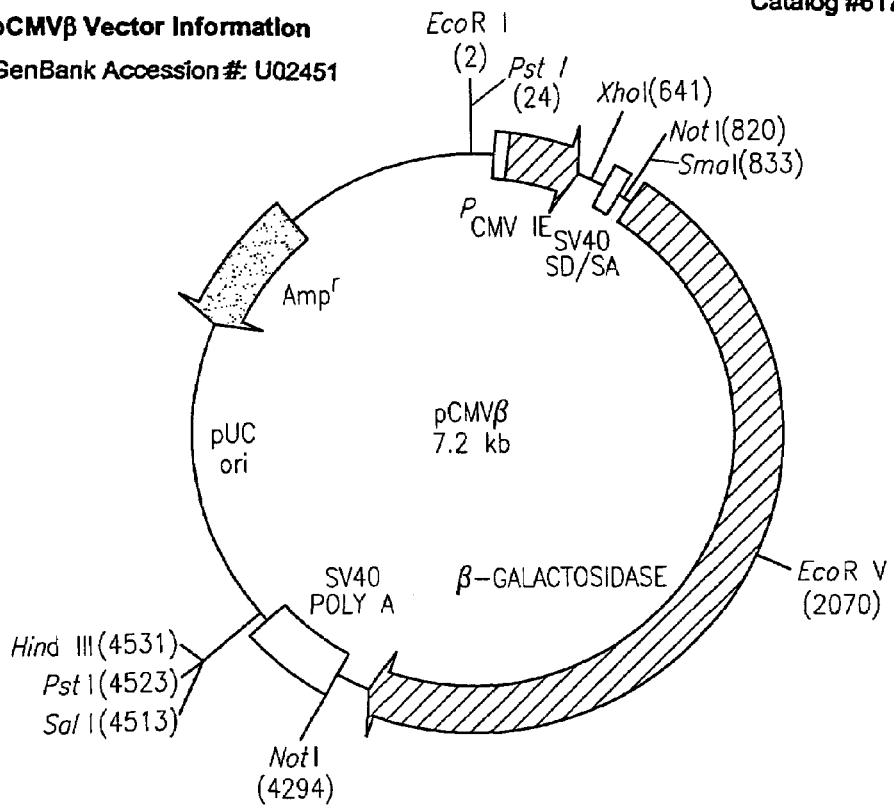

Fig. 8

Description pCMVβ is a mammalian reporter vector designed to expression β-galactosidase in mammalian cells from the human cytomegalovirus immediate early gene promoter (1). pCMVβ contains an intron (splice donor/splice acceptor; 2) and polyadenylation signal from SV40, and the full-length *E. coli* β-galactosidase gene with eukaryotic translation initiation signals (3). pCMVβ expresses high levels of β-galactosidase and can be used as a reference (control) plasmid when transfecting other reporter gene constructs and can be used to optimize transfection protocols by employing standard assays or stains to assay β-galactosidase activity. Alternatively, the β-galactosidase gene can be excised using the *Not* I sites at each end to allow other genes to be inserted into the pCMVβ vector backbone for expression in mammalian cells or to insert the β-galactosidase fragment into another expression vector.

lane 1: Sal I cut pSEAP-2 Control DNA
lane 2: Sal I cut pSEAP-2 Control DNA in Modified Tyrode's medium
lane 3: Sal I cut pSEAP-2 Control DNA + 0.1 µg mAb C
lane 4: Sal I cut pSEAP-2 Control DNA + 0.3 µg mAb C
lane 5: Sal I cut pSEAP-2 Control DNA + 1.0 µg mAb C
lane 6: Sal I cut pSEAP-2 Control DNA + 3.0 µg mAb C
lane 7: Sal I cut pSEAP-2 Control DNA + 10.0 µg mAb C
lane 8: Sal I cut pSEAP-2 Control DNA in Modified Tyrode's medium pSEAP2-Control Vector Information

GenBank Accession #: U89938

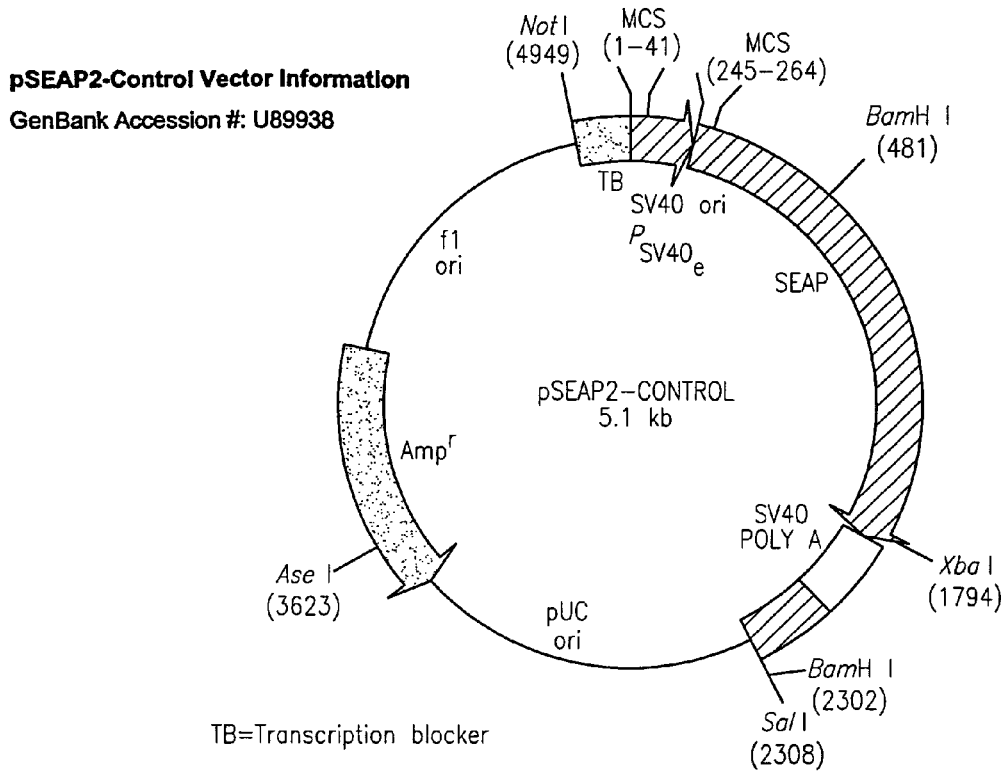

TB=Transcription blocker

Description:
pSEAP2-Control is a positive control vector expressing secreted alkaline phosphatase (SEAP) under the control of the SV40 early promoter and the SV40 enhancer. The SEAP coding sequence is followed by the SV40 late polyadenylation signal to ensure proper, efficient processing of the SEAP transcript in eukaryotic cells. A synthetic transcription blocker (TB), composed of adjacent polyadenylation and transcription pause sites, located upstream of the MCS reduces background transcription (1). The vector backbone also contains an f1 origin for single-stranded DNA production, a pUC origin of replication, and an ampicillin resistance gene for propagation and selection in E. coli. The SEAP2 Vectors incorporate a number of features that improve the sensitivity of SEAP by increasing the efficiency of SEAP expression or that enhance the utility of the vectors. These include: an improved Kozak consensus translation initiation site (2); the removal of the SV40 small-t intron, which can cause cryptic splicing and reduced expression in some genes and/or cell types (3, 4); switching from the early to late polyadenylation signal of SV40, which typically causes a five-fold increase in mRNA levels (5); an expanded multiple cloning site (MCS); compact plasmid size; and removal of extraneous sequences from the 3' untranslated region of the SEAP mRNA.

*Fig. 12*

VECTOR FOR GENETICALLY MODIFYING NON-HUMAN ANIMALS

FIELD OF INVENTION

The present invention relates to the field of genetic modification in non-human animals.

BACKGROUND OF THE INVENTION

Efficient genetic modification of animals, especially in higher mammals, has been a major goal of researchers in the biotechnology field for the last two decades. Not only can genetic modification of animals advance our understanding of genes and gene-functions in multi-cell organisms, it can also serve useful applications in the bio-agricultural industry. Examples of these applications include raising livestock with desired characteristics such as faster growth rate, production of therapeutic proteins in milk, or even the generation of more "humanized" organs from animals for use in animal to human xenotransplantation.

Current techniques to modify the genome include microinjection of foreign DNA into the pronuclei of fertilized eggs, delivery of foreign DNA into embryonic stem cells in vitro or blastomere cells in vivo through lipid-based agents, electroporation, or viral infection. Aside from mice, however, current techniques have been reported to have had limited success in higher or larger animals. The microinjection technique, for example, has been reported to be technically very demanding and requires the use of highly sensitive and expensive equipment. The viability of embryos after microinjection has also been reported to be very poor. Wall, R. J., et. al. (1992) Making Transgenic Livestock, Genetic Engineering on a Large Scale, *Journal of Cellular Biochemistry*, Vol. 49, pp. 113–120. This has led researchers in the field to investigate alternative and easier ways of delivering genes into an animal.

In 1989, Lavitrano, M., et. al. reported that simply incubating foreign DNA with mice's sperm cells and effecting fertilization in vitro could lead to genetically modified mice. Lavitrano, M., et. al. (1989) Sperm Cells as Vectors for Introducing Foreign DNA into Eggs-Genetic Transformation of Mice, *Cell*, Vol. 57, pp. 717–723. Characterized as the "cold fusion" equivalent in biotechnology, this report generated much excitement in the field. Birnstiel, M., et. al. (1989) Dangerous Liaisons: Spermatozoa as Natural Vectors for Foreign DNA?, *Cell*, Vol. 57, pp. 701–702. Those skilled in the art, however, are reported to remain skeptical even to this day about the Lavitrano's report since a number of researchers in the field have reportedly failed to repeat the experiment. Brinster, R., et. al. (1989) No Simple Solution for Making Transgenic Mice, *Cell*, Vol. 59, pp. 239–241; Smith, K. (1999) Sperm Cell Mediated Transgenesis: A Review, *Animal Biotechnology*, Vol. 10(1 &2), pp. 1–13.

Over the last decade, efforts have continued to explore the use of sperm cells as a vector for mediating gene transfer in animals. Researchers have elucidated that sperm cells have the inherent ability to internalize foreign DNA. Francolini, M., et. al (1993) Evidence for Nuclear Internalization of Exogenous DNA into Mammalian Sperm Cells, *Mol. Reprod. Devel.*, Vol. 34, pp. 133–139. Yet, certain inhibitory factors present in seminal fluid may inhibit this ability to take up DNA. Lavitrano, M., et. al. (1992) The Interaction Between Exogenous DNA and Sperm Cells, *Mol. Reprod. Devel.*, Vol. 31, pp. 161–169. In addition, foreign DNA introduced into sperm cells may also suffer from extensive DNA rearrangement because in mature sperm cells, internalization of foreign DNA may activate certain endogenous nucleases in these cells. Maione, B. et. al. (1997) Activation of Endogenous Nucleases in Mature Sperm Cells upon Interaction with Exogenous DNA, *DNA and Cell Biology*, Vol. 16, pp. 1087–1097. Such rearrangement could threaten the usefulness of genetically modified animals using this technique.

Other work with sperm cells as vector have focused on the use of either lipid-based agents or electroporation to deliver foreign DNA into the sperm cells. Smith, supra; Rottman R., et. al. (1996) Liposome-mediated Gene Transfer via Sperm Cells. High Transfer Efficiency and Persistence of Transgenes by Use of Liposomes and Sperm Cells and a Murine Amplification Element, *Journal of Animal Breeding and Genetics*, Vol. 113, pp. 401–411; PCT Publications WO 99/42569, WO 99/40213, and WO 97/11597. Such methods may also suffer from the same problem of DNA internalization and exposure to nucleases that could cause rearrangement of the foreign DNA being introduced. In addition, lipid-based agents, which are often toxic, and electroporation may require extensive experimentation to prevent the death or the loss of sperm cell motility. Other techniques have also focused on using recombinant virus infection, as disclosed in PCT Publications WO 99/38991, or on using a "gene gun" with micro-carriers, as disclosed in PCT Publication WO 93/24626, to introduce foreign DNA into sperm cells. Such techniques may be technically challenging and may also affect the viability and motility of the sperm cells. They may also suffer from the same problem of DNA internalization and exposure to nucleases that could cause rearrangement of the foreign DNA being introduced.

Since 1989, researchers have reported the use of sperm cells as vectors in different animals ranging from insects, marine animals, amphibians, birds, and mammals. Smith, supra. However, few reported that the genetic modification was observed in viable mature offspring. Smith, supra. More problematic is the fact that some reports used only PCR analysis to verify the existence of the foreign DNA in the cells. These reports are summarized in table one of Gandolfi, F. (1998) Spermatozoa, DNA Binding and Transgenic Animals, *Transgenic Research*, Vol. 7, pp. 147–155. Since PCR cannot distinguish between foreign DNA transmitted through episomes or through the chromosomal DNA, Gandolfi has questioned the value of these reports stating that it "opens up an important argument relating to appropriate evaluation of the results described in some reports." Gandolfi, supra. Episomal transmission is not as desirable as chromosomal transmission since the episome may be lost during subsequent cell division, and the desired effect of genetic modification may never be expressed in adult animals.

Because an easy, non-toxic, and efficient way of genetically modifying animals, especially in higher mammals, can greatly advance this field, a new way of using sperm cells for delivering genes into animals is needed.

SUMMARY OF THE INVENTION

The present invention is directed to a vector and its use to generate genetically modified animals and cells. One aspect of this invention involves a vector that comprises a sperm cell and one or more polynucleotide molecules bound to a sperm cell through one or more non-liposome based linkers. The sperm cell can be any animal sperm cell, preferably non-human animal. In one preferred embodiment of this invention, the one or more polynucleotide molecules encode for a gene product that confers desired characteristics in the cells or the animals. In another preferred embodiment of this invention, the linker is a protein or polypeptide, preferably a sperm specific linker that binds with the external surface of the sperm cell. The linker interacts with one or more polynucleotide molecules preferably by ionic interaction. This interaction can also be carried out by different molecular interactions, including the use of another or secondary linker. The association of the sperm, linker, and the one or more polynucleotide can also occur in vitro or in vivo.

In another aspect of the present invention, genetically modified cells or animals are derived from the fertilization of an animal egg cell with the vector described above. Fertilization can occur in vitro or in vivo. In one preferred embodiment, genetic modification occurs with the polynucleotide molecule integrating, wholly or partially, into the cell or animal's genome. Another aspect of the present invention includes cells, such as sperm cells or egg cells, and cell lines that are derived from these genetically modified animals or their descendants.

In another aspect of the present invention, the genetically modified animals derived from the use of the sperm vector described above possess certain desired characteristics. Examples of these characteristics include faster growth rates, disease or pathogen resistance, high production of certain proteins in milk, and organs suitable for animal to human xenotransplantation.

BRIEF DESCRIPTION OF THE DRAWINGS

FIG. 8 shows a plasmid map of pCMV-β.

FIG. 12 shows the plasmid map of pSEAP-2-control.

GENERAL DESCRIPTION OF THE INVENTION

Figure 1:
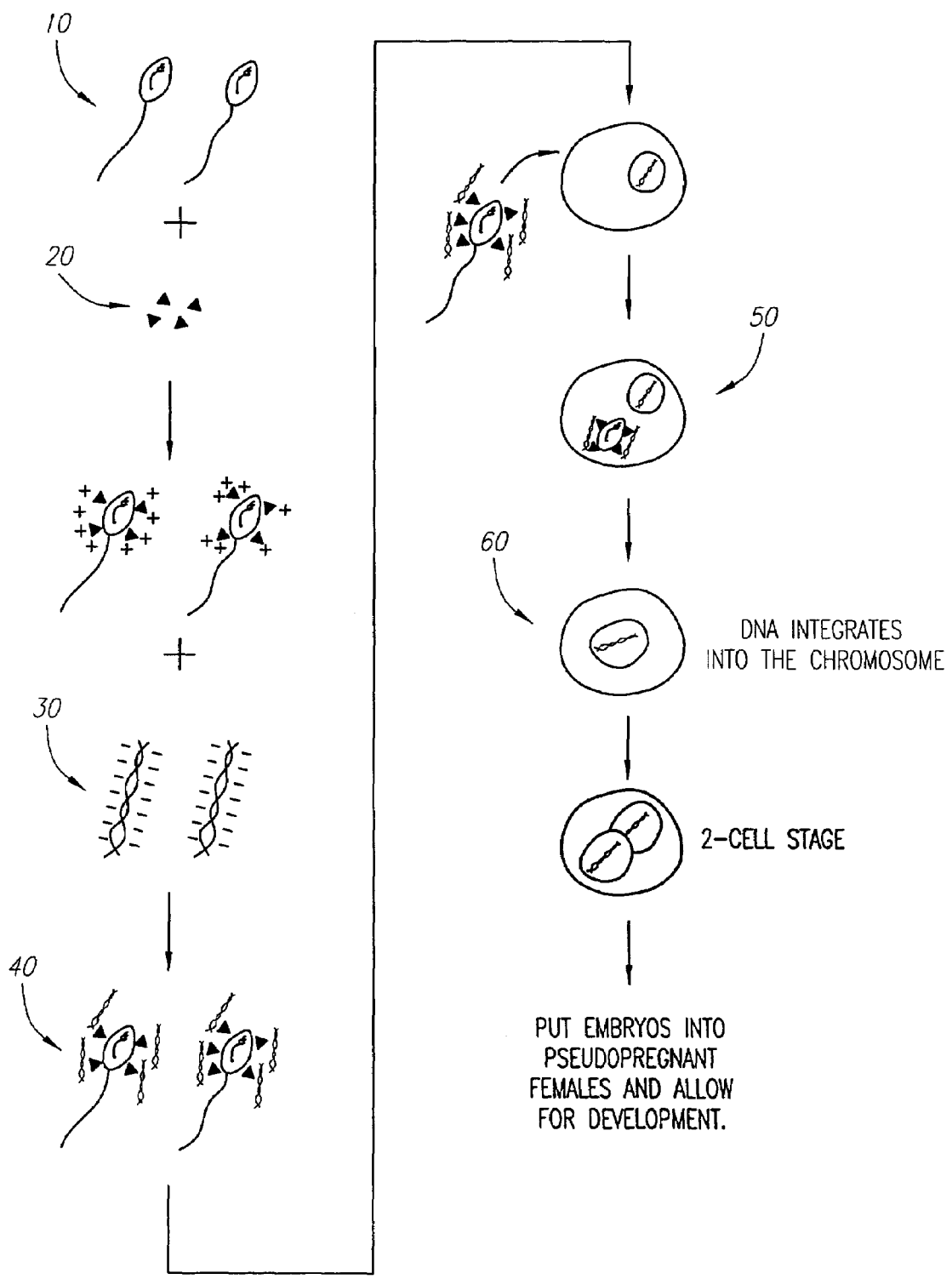
FIG. 1 is a pictorial representation of the basic steps involved in using one embodiment of the present invention.

Generally, FIG. 1 shows the basic steps involved in using one embodiment of the present invention to genetically modify cells or animals using a sperm vector. Briefly, animal sperm cells 10, are collected by methods known in the art or purchased commercially from sources such as Birchwood Genetics in West Manchester, Ohio, and are bound together with linkers 20. These linkers are preferably antibodies or immunoglobulins of the types, IgG, IgA or IgM, but they can also be other compounds such as peptides, glycoproteins, carbohydrates, or other chemical-compound linkers. These linkers bind or associate to the sperm cells' external surface through different molecular interactions such as ionic interaction, covalent bonds, Vander Waals forces, or ligand-receptor interaction. Circular or linear DNA molecules 30 then bind or attach to the linkers on the sperm-linker complex also through different molecular interactions such as ionic, covalent bonds, Vander Waals forces, or ligand-receptor interaction. These DNA molecules may encode for certain gene products, but they may also be disrupted genes, homologous with endogenous genes, that recombine into the chromosome to knockout a gene. The sperm-linker-DNA complex 40 formed can then be used to effectuate fertilization in vitro or in vivo. Upon fertilization, the DNA is introduced into the fertilized egg 50 and embryo 60 and can integrate into the chromosome, becoming a part of an animal or cell's genetic material.

Alternatively, the binding, coupling, linking, attaching, or association of the sperm-linker-DNA complex can also be accomplished in vivo. The linker and the DNA can first be coupled or bound together in vitro. Afterwards, this linker-DNA complex can be injected directly or indirectly into a male animal's testicles. PCT Publications WO 99/40213 and WO 97/11597 disclose procedures for injecting DNA into the testicles, and these publications are incorporated herein by reference.

An example of a linker-DNA complex is an antibody attached with DNA molecules where the antibody specifically recognizes certain surface epitopes on sperm cells. Because of the acidic characteristic of naked DNA, it can ionically associate, bind or, couple with an antibody that has basic or positively charged properties. However, the DNA-linker interaction is not limited to ionic interaction. The complex can also be crosslinked by UV light to form covalent bonds by well known methods in the art. Both the DNA and the linker can also be modified by methods known in the art. For example, the DNA can be biotinylated by adding biotinylated deoxynucleotides in a PCR reaction; the antibody can be modified or purchased with attached streptavidin, which binds tightly to the biotin on the DNA; or a secondary antibody, which is modified with streptavidin and recognizes the first antibody can also act as a secondary linker between the modified DNA and the first linker.

If the DNA-linker complex is injected into the testis of the animal, this complex can seek out the sperm cells and bind to them. Fertilization can then occur in vivo via either natural copulation of the male and female animals or by artificial insemination of the female with collected sperm cells. The collected sperm cells can also be used with in vitro fertilization techniques, which are well known in the art. On the other hand, if binding of the sperm-linker-DNA complex, as a whole, occurred in vitro, fertilization can be achieved by in vitro fertilization techniques. The fertilized eggs and resulting embryos can then be transplanted to surrogate-animal mothers for development. Alternatively, well known artificial insemination methods or injections of the sperm-linker-DNA complex directly into the oviduct of female animals can also achieve fertilization in vivo.

Genetically modified animals can serve a number of useful applications. Livestock, poultry, or fish can be inserted with genes that encode for growth hormones to make them grow faster than normal or they can also be inserted with the somatotropin gene to increase muscle growth and decrease adipose tissue. Pursel, V. G., et. al. (1989) Genetic Engineering of Livestock, *Science*, Vol. 244, pp. 1281–1288; Etherton, T. D., et. al. (1993) Mechanism by which Somatotropin Decreases Adipose Tissue Growth, *American Journal of Clinical Nutrition*, Vol. 58 (Supp.), pp. 287S–295S. Inserting genes such as interferon that boost the immune system or other genes, such as genes encoding for viral, prion, or bacterial proteins, can also make these livestock, poultry, or fish disease or pathogen resistant. Examples of these infectious pathogens include *Salmonella*, influenza virus, prion proteins for the Mad Cow Disease, etc. Alternatively, introducing DNA encoding for anti-sense RNA molecules, which are complementary to these viral, prion, or bacterial RNAs, may also inhibit translation and production of proteins from these RNA, which limits growth and spread of these infectious pathogens.

Moreover, in animals, including insects such as silkworms, that produce raw materials for clothing such as wool and silk, inserting genes for biochemical enzymes that produce the rate-limiting amino acid may increase production of these raw materials. In sheep, for example, the availability of the amino-acid cysteine limits the production of wool. Inserting bacterial genes that encode for serine transacetylase and O-acetylserine sulfhydrylase may increase the conversion of serine and acetyl-CoA into cysteine, which in turn may increase production of wool. Ward, K., (1991) The Application of Transgenic Techniques for the Improvement of Domestic Animal Productivity, *Current Opinion in Biotechnology*, Vol. pp. 834–839.

Furthermore, these genetically modified animals can also produce therapeutic proteins, such as insulin, growth hormone, interferon, erythropoietin, colony stimulating factor (GM-CSF), t-PA, or factor VIII, in their milk by joining the genes for these proteins with promoters from mammary specific genes such as sheep's β-lactoglobulin, mouse whey acid protein, or bovine αS1-casein. Id. On the other hand, the animal's milk can also be fortified with addition of humanized proteins, such as human lactoferrin that enhance the intestinal iron absorption in infants. Lonnerdal, B. (1996) Recombinant Human Milk Proteins—An Opportunity and a Challenge, *American Journal of Clinical Nutrition*, Vol. 63, pp. 622–626. Genetically modified pigs can even be a source for more "humanized" organs in animal to human xenotransplantation using genes such as human decay accelerating factor. Cozzi, E., et. al. (1994) Expression of Human Decay Accelerating Factor in Transgenics Pigs, *Transplantation Proceedings*, Vol. 26, pp. 1402–1403.

The articles cited above are all incorporated herein by reference.

The following examples demonstrate that the inventor has produced a number of genetically modified animals using the sperm vector as described above. Methods in molecular genetics, flow cytometry, antibody production, hybridoma technology, in vitro fertilization, embryo manipulation, and artificial insemination used but not explicitly described in this disclosure had already been amply reported in the scientific literature. These methods are well within the ability of one skilled in the art.

EXAMPLE I

This example illustrates the preparation of an antibody specific to sperm cells.

Sperm cells collected from male mice were injected back into mice as antigens to immunize and produce antibodies reactive to sperm-surface antigens. Monoclonal antibodies, developed using common hybridoma techniques, were screened using flow cytometry to identify candidate antibodies that will bind to a series of different animals (mouse, pig, cow, sheep, goat, and chicken). Briefly, sperm cells were incubated with the different primary monoclonal antibodies, washed, and further incubated with a secondary antibody that specifically recognized mouse immunoglobulin. This secondary antibody, which was commercially available and well known in the art, had fluorescent molecules such as fluorescein or rhodamine conjugated to it. Once the secondary antibody molecules were bound and washed, the flow-cytometry instrument or the FACS sorter counted the number of fluorescent sperm cells with bound primary and secondary antibodies from naked sperm cells.

FIGS. 2–7 show these flow-cytometry analyses for mAbC which is secreted from the hybridoma cell line assigned the deposit designation number PTA-6723, deposited on May 24, 2005 with the American Type Culture Collection, 10801 University Boulevard, Manassas, Va. 20110-2209, that bind to sperm cells of mouse, pig, cow, chicken, goat, and sheep, respectively. The Y-axis corresponds to the number of sperm cells detected while the X-axis is the relative intensity of fluorescence bound to the cell. Cross-lined peaks denote control reactions where the sperm cells were incubated only with the fluorescent anti-mouse immunoglobulin antibody. On the other hand, the shaded peaks denote the reactions where mAbC antibody and the secondary antibody were incubated with corresponding sperm cells in a mouse, pig, cow, chicken, goat, and sheep, respectively. Right shifts in the peaks denote positive binding of the mAbC antibody.

Figure 2:
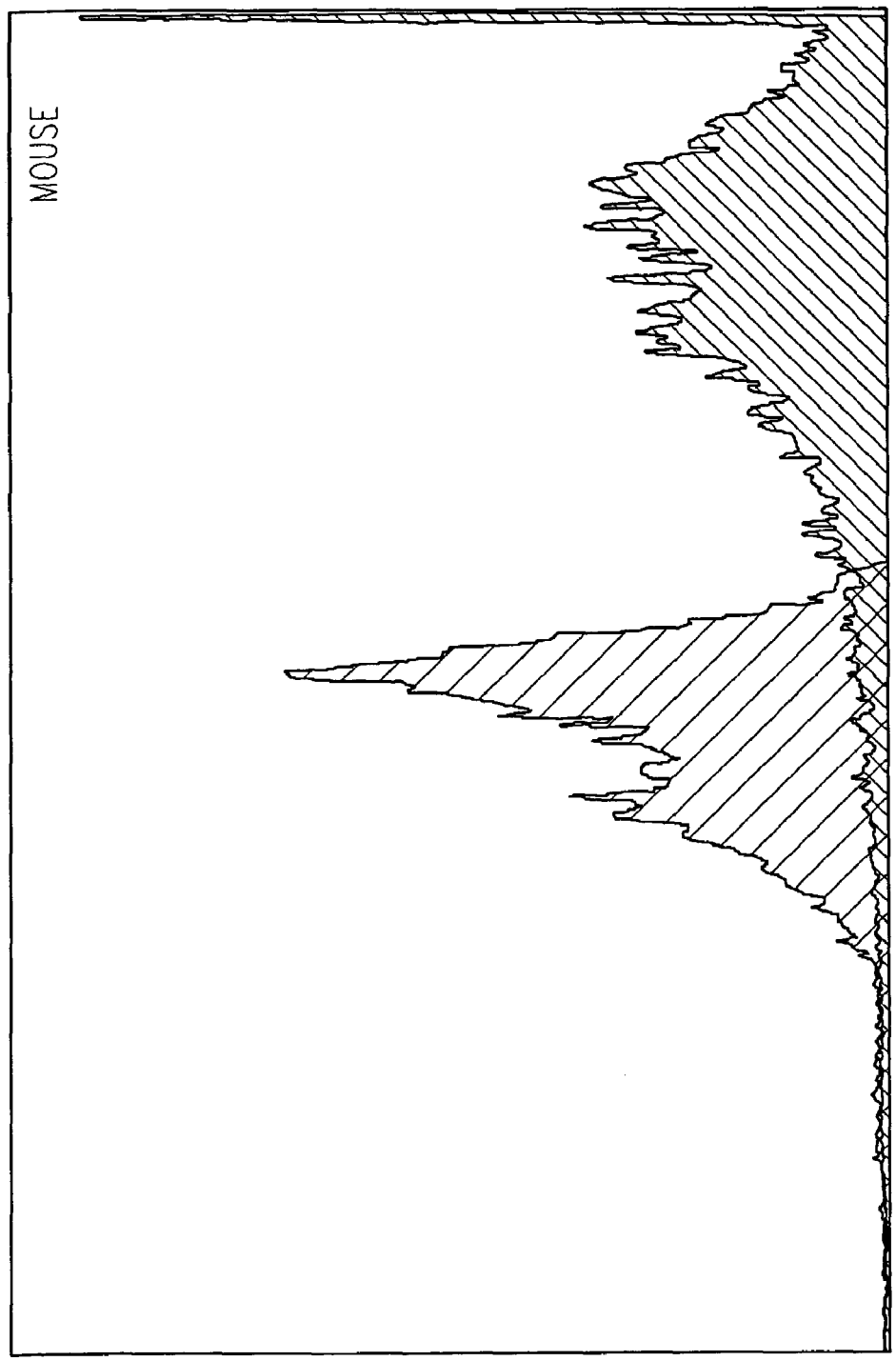
FIG. 2 shows a flow-cytometry result of binding a sperm-specific antibody to mice's sperm cells as embodied in one aspect of the present invention.
Figure 3:
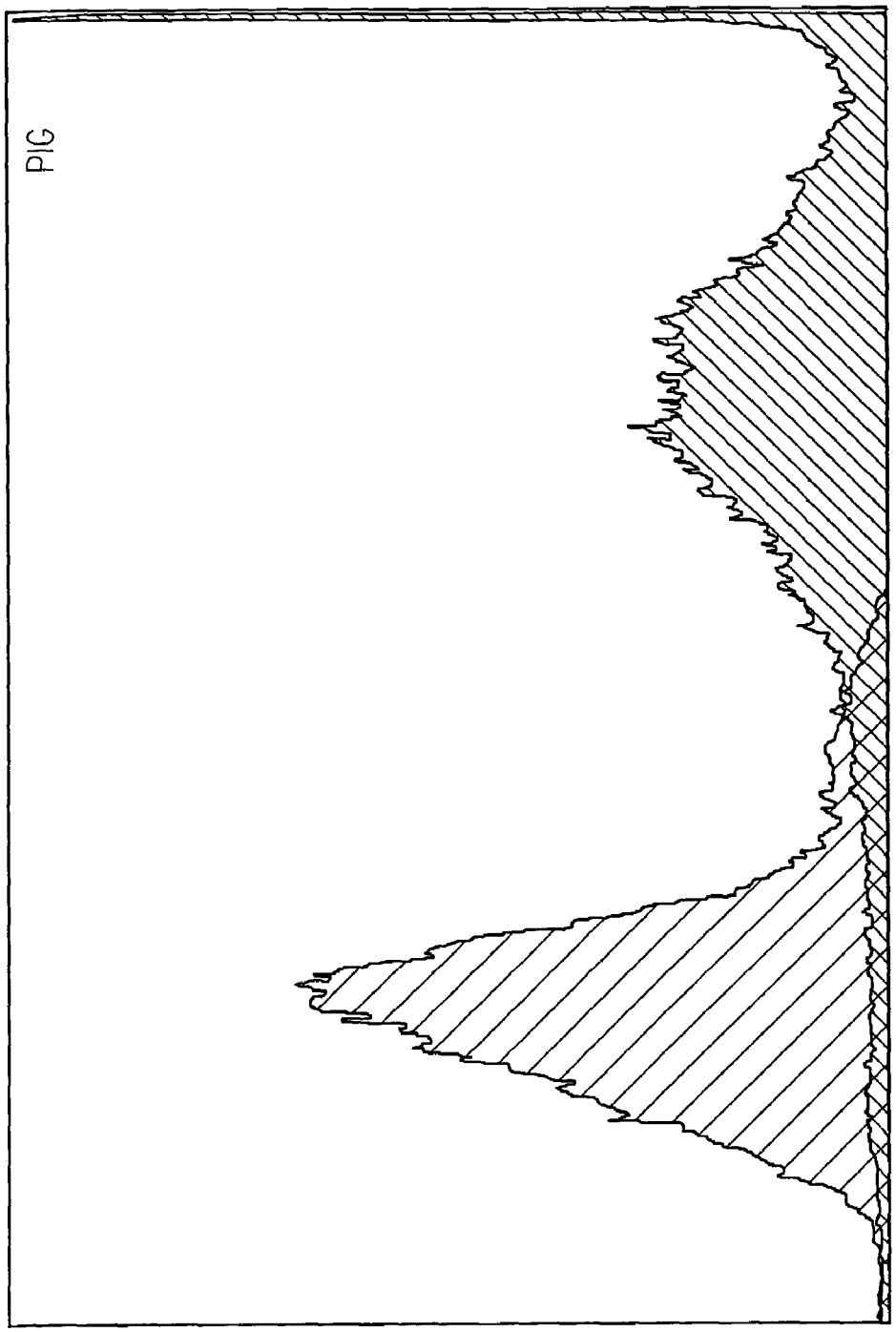
FIG. 3 shows a flow-cytometry result of binding a sperm-specific antibody to pig's sperm cells as embodied in one aspect of the present invention.
Figure 4:
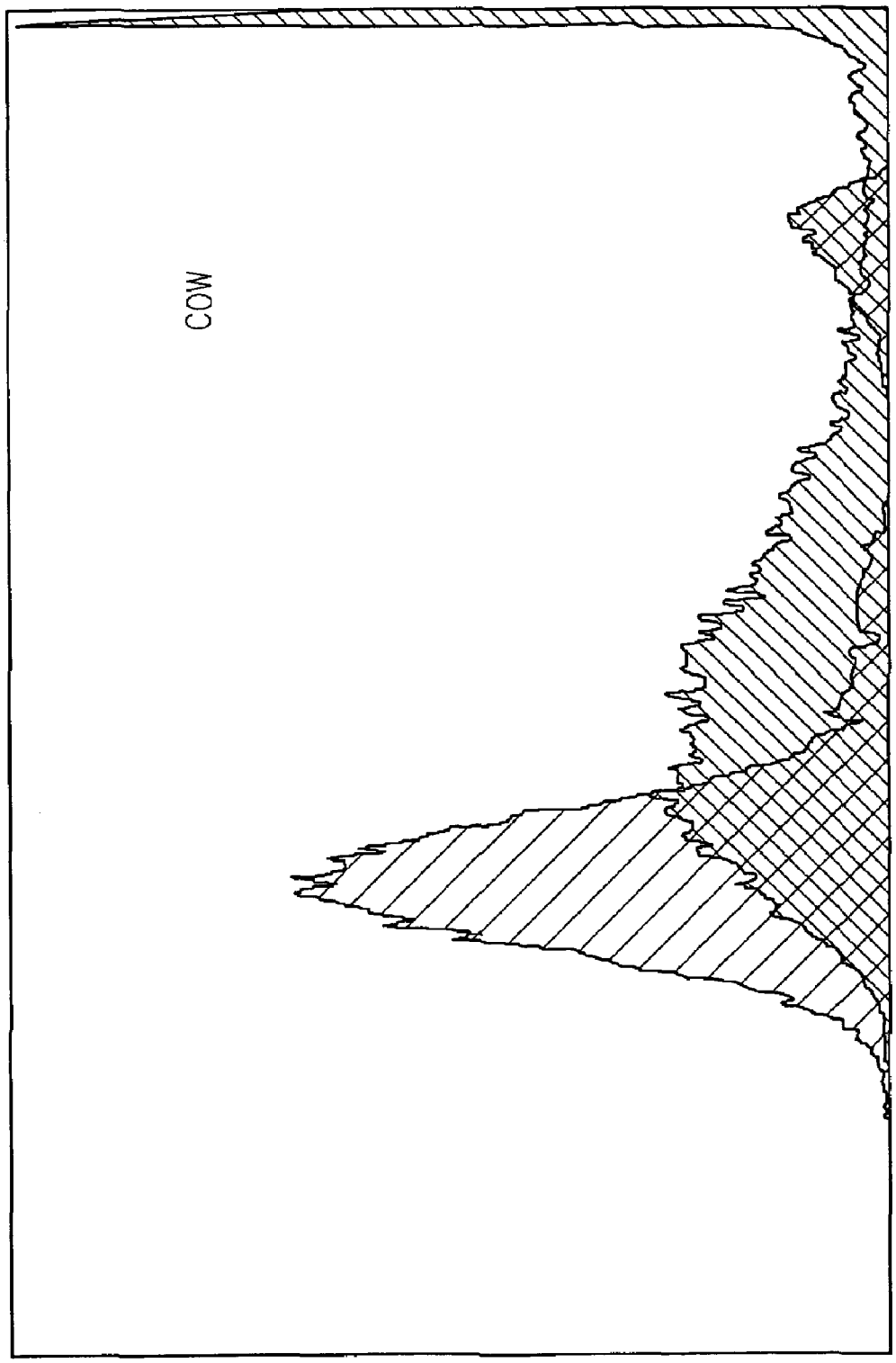
FIG. 4 shows a flow-cytometry result of binding a sperm-specific antibody to cow's sperm cells as embodied in one aspect of the present invention.

As can be seen in FIG. 2, greater fluorescence signals can be detected from mouse sperm cells incubated with mAbC and the fluorescent secondary antibody compared with sperm cells incubated with fluorescent secondary antibody alone. Similarly, in FIGS. 3 and 4, greater fluorescence can be detected from pig and cow sperm cells, respectively, incubated with mAbC and the fluorescent secondary antibody as evidenced by the right shaded peaks.

Figure 5:
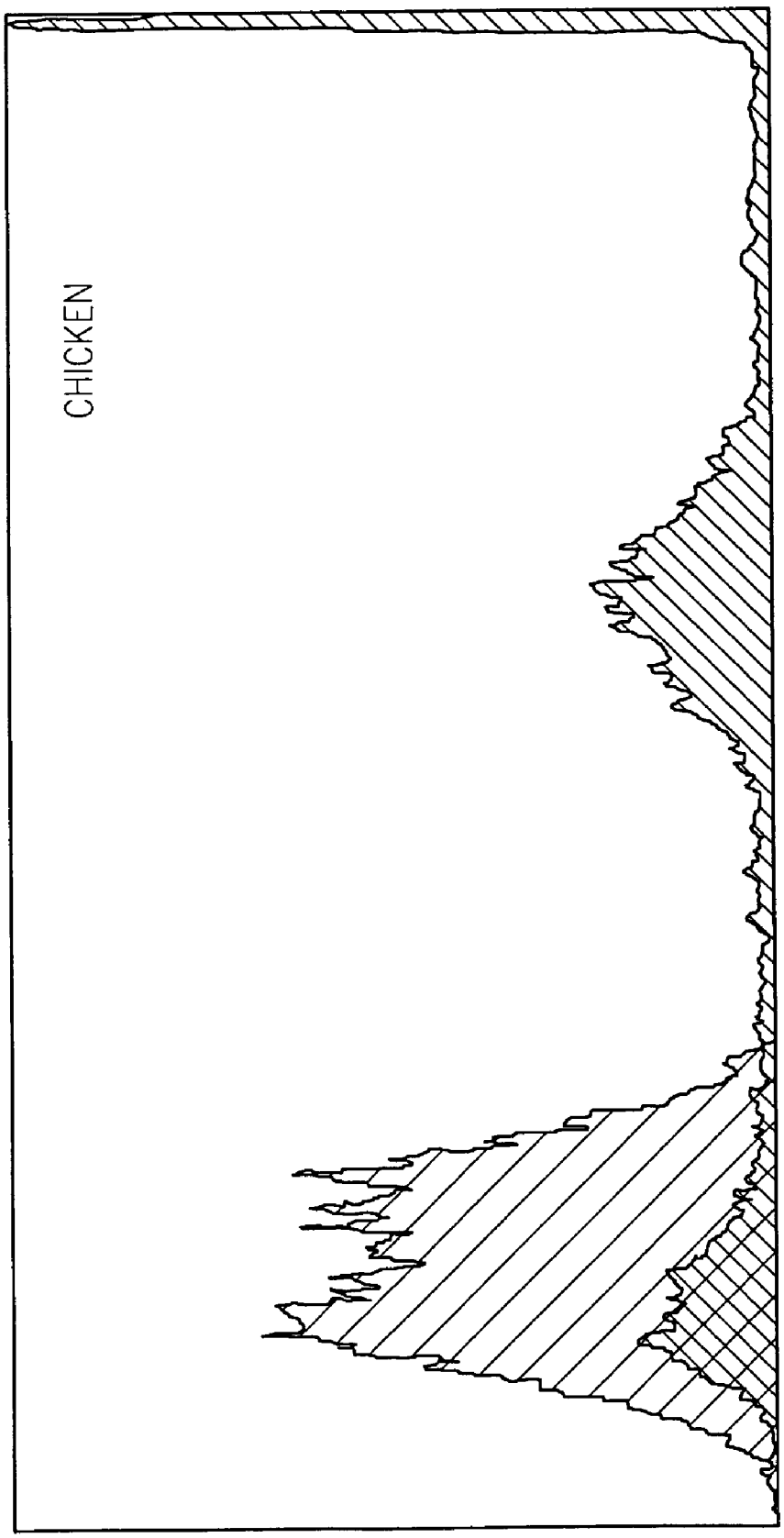
FIG. 5 shows a flow-cytometry result of binding a sperm-specific antibody to chicken's sperm cells as embodied in one aspect of the present invention.

In FIG. 5, the incubation of the fluorescence antibody alone with the chicken sperm cells did not result in any fluorescence being detected in these sperm cells. In contrast, the right peak signified fluorescence in the chicken sperm cells that have attached mAbC antibodies. FIG. 5 also shows that some population of chicken sperm cells may not express the antigen recognized by mAbC as evidence by the left shaded peak.

Figure 6:
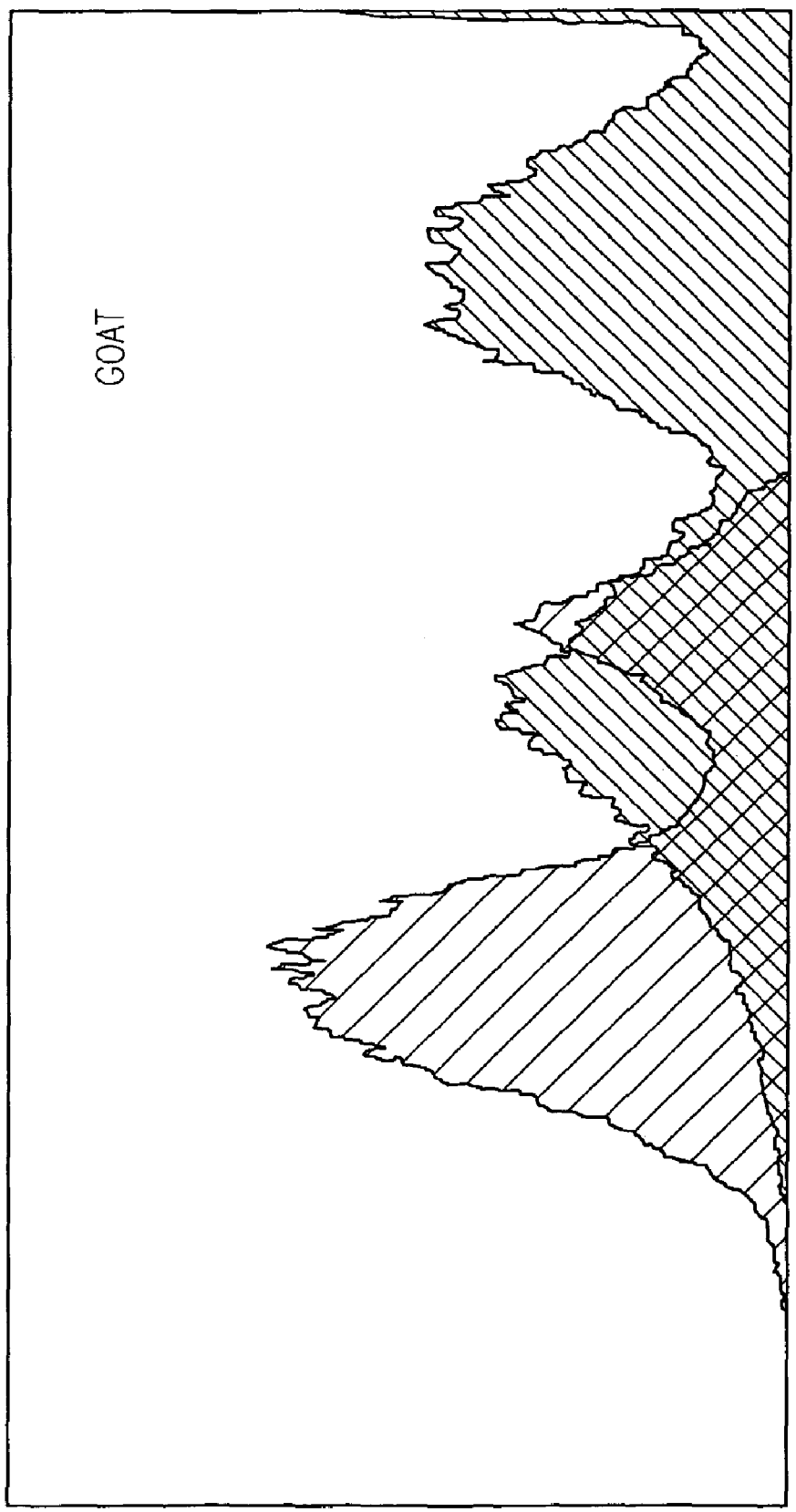
FIG. 6 shows a flow-cytometry result of binding a sperm-specific antibody to goat's sperm cells as embodied in one aspect of the present invention.

In FIG. 6, fluorescence can be detected from goat sperm cells incubated with mAbC and the fluorescent secondary antibody as evidenced by the two right shaded peaks. The left shaded peak may suggest a population of the goat sperm cells that express the antigen recognized by mAbC at a lower level than the population in the right peak. In contrast with the chicken sperm cells incubated with only the fluorescent secondary antibody in FIG. 5, the anti-mouse immunoglobulin fluorescent antibody seems to also bind to the goat sperm cells, but at a much reduced level than with mAbC acting as a linker.

Figure 7:
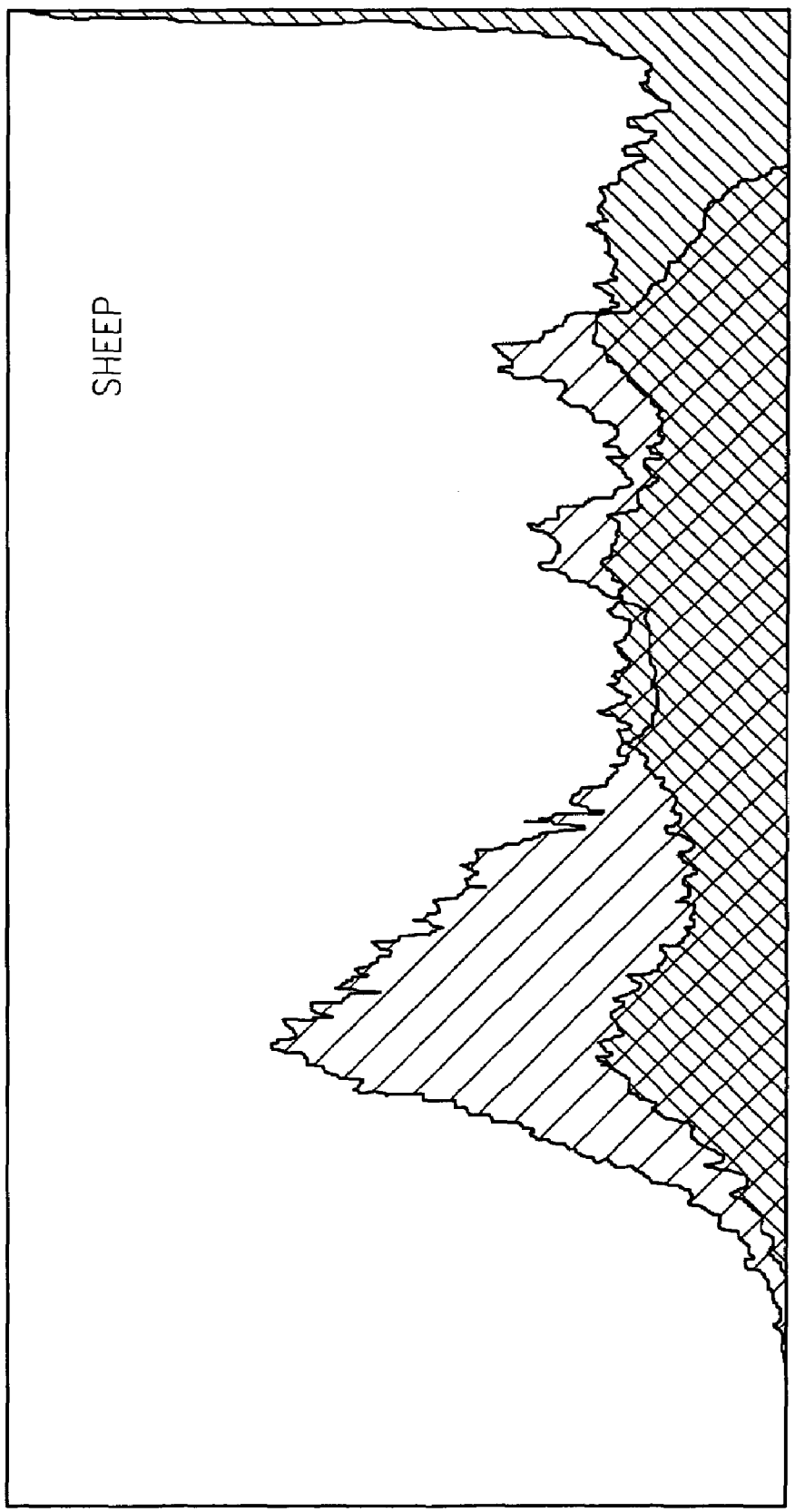
FIG. 7 shows a flow-cytometry result of binding a sperm-specific antibody to sheep's sperm cells as embodied in one aspect of the present invention.

Similarly, in FIG. 7, fluorescence can be detected from sheep sperm cells incubated with mAbC and the fluorescent secondary antibody as evidenced by the right shaded peaks. The distribution of the peaks again suggests the possibility that different sperm cells have different levels of the antigen recognized by mAbC. As seen in FIGS. 2, 3, 4, 6, and 7, mammalian sperm cells bind, at some lower level, to the fluorescent secondary antibody. Since the secondary antibody is directed to a mouse immunoglobulin, it may have cross reactivity to other mammalian proteins on the sperm cell surfaces, which are not present in the chicken sperm cells (FIG. 5). Nevertheless, the shifts in fluorescence peaks upon addition of mAbC clearly demonstrate the higher affinity of the mAbC antibody to different animal sperm cells.

EXAMPLE II

This example illustrates the ability of the monoclonal antibody mAbC to bind to DNA molecules through ionic interaction.

Different volumes of purified solutions of mAbC at a concentration of 0.5 mg/ml were added to DNA solutions containing 300 ng of Sal I cut pCMV-β plasmid (FIG. 8, Clontech Laboratories, Inc., Cat. # 6177-1). After incubating the mixtures at room temperature for forty minutes, the mixtures were loaded on a regular one percent agarose gel and run at 20 milli-amps for one hour. Afterwards, the DNA was stained with Ethidium Bromide and visualized under UV light.

Figure 9:
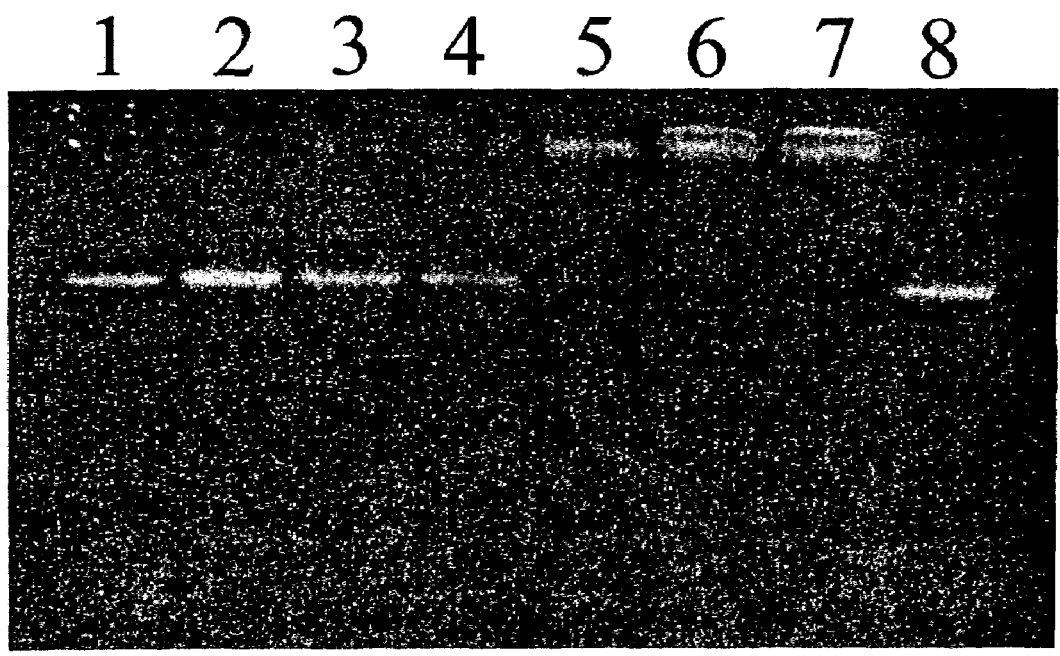
FIG. 9 shows an agarose-gel analysis of a sperm-specific antibody binding to pCMV-β plasmid.

In FIG. 9, lanes 1, 2, and 8 were controls with lane 1 being pure Sal I cut pCMV-β plasmid and lanes 2 and 8 being Sal I cut pCMV-β plasmid in Modified Tyrode's medium. Lanes 3, 4, 5, 6, and 7 corresponded to experimental reactions with the Sal I cut pCMV-β plasmid incubated with 0.2 µl, 1 µl, 2.5 µl, 6 µl, and 10 µl of mAbC at 0.5 mg/ml. In lanes 5, 6, and 7, increasing amounts of DNA were retained in the wells of the gel, showing that association of the antibody, which has a positive charge, with the plasmid DNA, which has a negative charge, yielded a net electric charge of zero, resulting in a complex that no longer responds to the electric field in the gel.

EXAMPLE III

This example illustrates the binding or coupling of the DNA to the sperm via the linker or antibody.

DNA molecules, labeled with $p^{32}$ using standard end labeling techniques with T4 DNA polymerase, were incubated with mouse, pig, chicken, sheep, goat, and cow sperm cells together with either mAbC, mAbD, or a control antibody specific to a *Drosophila* protein. The amount of DNA binding was measured by scintillation counting. The ratio of sperm cells to antibody were as follows:

Mouse—400 thousand sperm cells to 600 ng of labeled DNA;

Pig—600 thousand sperm cells to 800 ng labeled DNA;

Chicken—300 thousand sperm cells to 500 ng of labeled DNA;

Sheep—1 million sperm cells to 500 ng of labeled DNA;

Goat—1 million sperm cells to 500 ng of labeled DNA; and

Cow—1 million sperm cells to 500 ng of labeled DNA.

Table 1 shows that with the presence of mAbC and mAbD, sperm cells significantly bound more labeled DNA compared with reactions with no antibody or with the Drosophila protein-specific antibody. Reactions 1 and 2 contained only sperm cells and labeled DNA, while reactions 3 and 4 contained the Drosophila-protein-specific antibody together with sperm cells and labeled DNA. Reactions 5 contained mAbD while reactions 6 and 7 contained mAbC together with sperm cells and labeled DNA.

TABLE 1

| Reactions | | Mouse (cpm) | Pig (cpm) | Chicken (cpm) | Sheep (cpm) | Goat (cpm) | Cow (cpm) |
|---|---|---|---|---|---|---|---|
| 1 | no antibody | 12471 | 12971 | 5830 | 15367 | 17749 | 12766 |
| 2 | no antibody | 15814 | 13713 | 6383 | 13259 | 16574 | 14398 |
| 3 | Control Antibody | 11541 | 10531 | N/D | 14018 | 155347 | 15351 |
| 4 | Control Antibody | 13653 | 14038 | N/D | 12834 | 15997 | 13918 |
| 5 | mAbD | 18900 | 16220 | 10314 | N/D | N/D | N/D |
| 6 | mAbC | 18139 | 16269 | 7294 | 19368 | 20385 | 20417 |
| 7 | mAbC | 19314 | 17343 | 9865 | 18437 | 19543 | 18643 |

N/D = Not determined

EXAMPLE IV

This example illustrates the procedures carried out to generate genetically modified mice.

Sperm cells were collected from dissected epididymis of nine to twenty weeks old FVB male mice. Cut into small pieces, these epididymis tissues were incubated in 300 µl of Modified Tyrode's medium at pH 7~8 for one hour to allow the sperm cells to escape into the medium. Once the sperm cells were collected in 300 µl of medium, five micrograms of the linker antibody were added to one million sperm cells at 37° C. for one hour. The sperm-linker complex was washed three times with 300 µl of Modified Tyrode's medium using a standard microcentrifuge set at 3000 rpm for one and a half minutes. The sperm-linker complex was finally resuspended in 300 µl of medium, and one microgram of linearized pCMV-β plasmid or a plasmid encoding for Hepatitis B surface antigen (HBsAg) was added and incubated for one hour.

To collect ovulated eggs, nine to twelve weeks FVB female mice each received an injection of 5 I.U. Pregnant Mares Serum (PMS) four days before the collection date and another 5 I.U. of human chorionic gonadotropin (hCG) two days before the collection date. Dissected ovulated eggs surrounded by cumulus cells were placed in a 35-mm petri dish containing a drop of Modified Tyrode's medium at room temperature. Afterwards, 300 µl of sperm-linker-DNA complex prepared as described above were added directly to the ovulated eggs. The whole mix was equilibrated with $CO_2$ at 37° C. with mineral oil added on top to prevent evaporation. After four hours of in vitro fertilization at 37° C., fertilized eggs were collected with capillary tubes and washed thrice with CZB medium. The embryos were further incubated in 300 µl of CZB medium for 20–22 hrs before being transferred to oviducts of pseudo-pregnant female mice.

Figure 10:
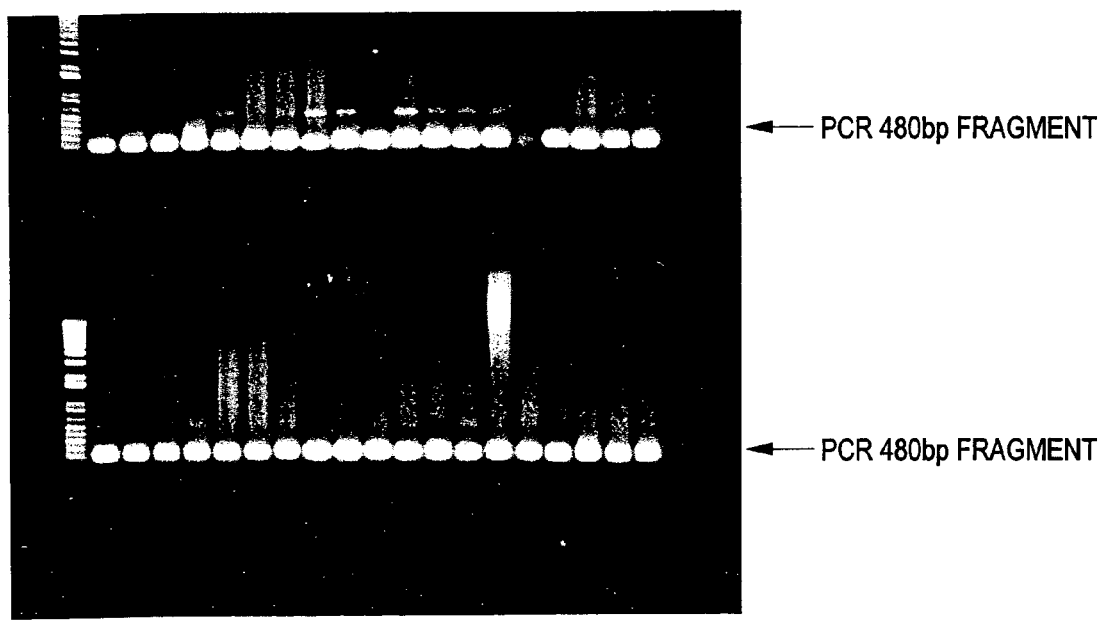
FIG. 10 show results of PCR analysis for the detection of pCMV-β sequences in genomic DNA isolated from mice's embryos genetically modified according to one embodiment of the present invention.

To confirm the presence of the pCMV-β plasmid, genomic DNA isolated from embryos, ten days after transplantation into the pseudo-pregnant female mice, were analyzed by PCR using primers that detect a 480 bp fragment corresponding to the CMV promoter region of the pCMV-β plasmid (FIG. 8). In FIG. 10, lanes 6, 7, 8, 9, 10, 12, 13, 14, 15, 17, 18, 19, 24, 33, and 40 clearly show this 480 bp PCR fragment. Lanes 1 and 21 corresponded to the molecular size markers.

Figure 11:
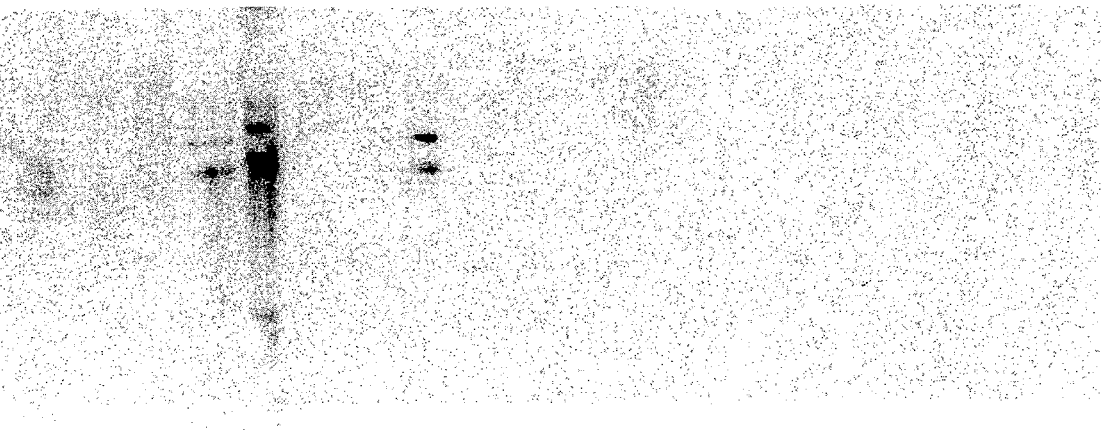
FIG. 11 shows results of southern-blot analysis for the detection of Hepatitis B surface-antigen gene-sequence in mice-tail-genomic DNA with this gene-sequence being integrated into the mice's chromosome according to one embodiment of the present invention.

To confirm integration of the HBsAg plasmid into the mice genome, southern blot analysis were also performed. Genomic DNA isolated from mice's tails were digested, ran on a gel, transferred to a nylon membrane according to methods known in the art. FIG. 11 shows the southern blot hybridization results with complementary probe sequences to HBsAg. Lanes 1–13 contained genomic DNA from mice born from pseudo-pregnant mice that received embryos fertilized with the sperm-linker-DNA complex described above; lanes C1–C7 contained genomic DNA from mice that were untreated or non-transgenic mice. Lanes 4, 5, and 8 show bands positive for HBsAg sequences integrated in the mice's genome, thus, demonstrating that three out the thirteen mice were genetically modified.

EXAMPLE V

This example illustrates the procedures carried out to generate genetically modified pigs.

Ejaculated sperm cells from pigs were collected using methods generally known in the art of animal husbandry. Suspended in one milliliter of pig extender medium (purchased from Merck, Germany, Ref.N.R.13515/0001—dilute mixture M3 for boar sperm), fifteen million sperm cells were incubated with five micrograms of the linker antibody for forty minutes at room temperature with intermittent shaking in between. After washing the sperm-linker mixture once with pig extender medium and finally resuspending the mixture in 1.5 ml of the same medium, five micrograms of the plasmid pSEAP2-control (FIG. 12, Clontech Laboratories, Inc., Cat. # 6052-1) were added and incubated with the mixture for forty minutes at room temperature. Direct injections of 200 µl of the resulting sperm-linker-DNA complex into the oviducts of anesthetized female pigs resulted in fertilization in vivo.

Figure 13:
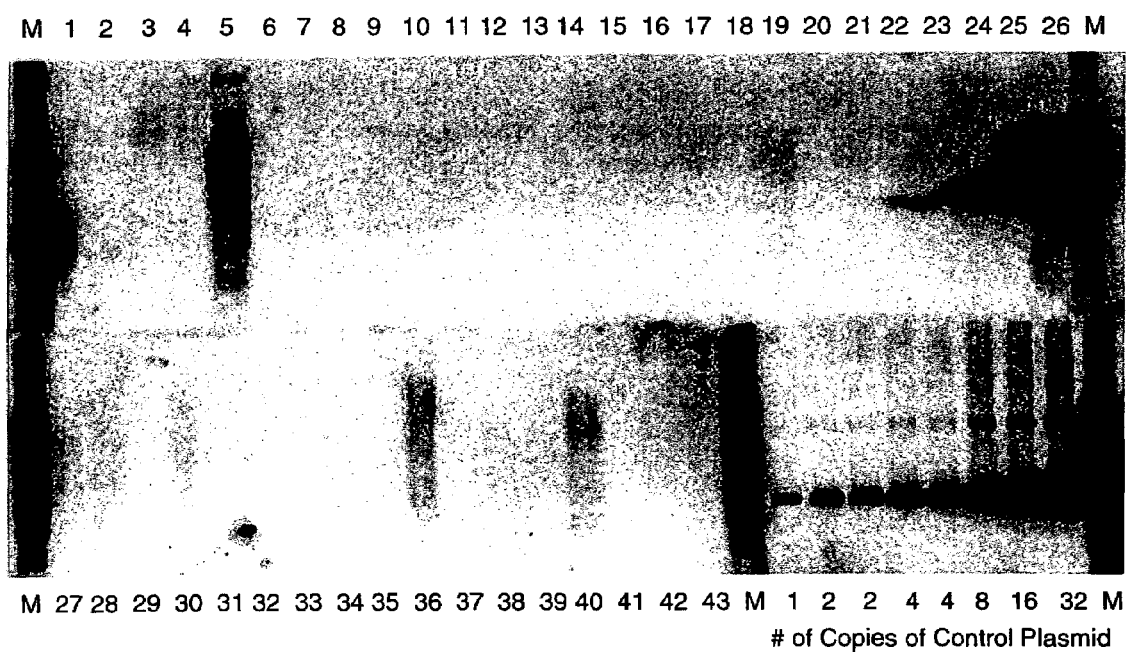
FIG. 13 shows the result of southern-blot analysis for the detection of pSEAP2-control plasmid sequence in the genomic DNA isolated from tail tissues of genetically modified pigs according to one embodiment of the present invention.
Figure 14:
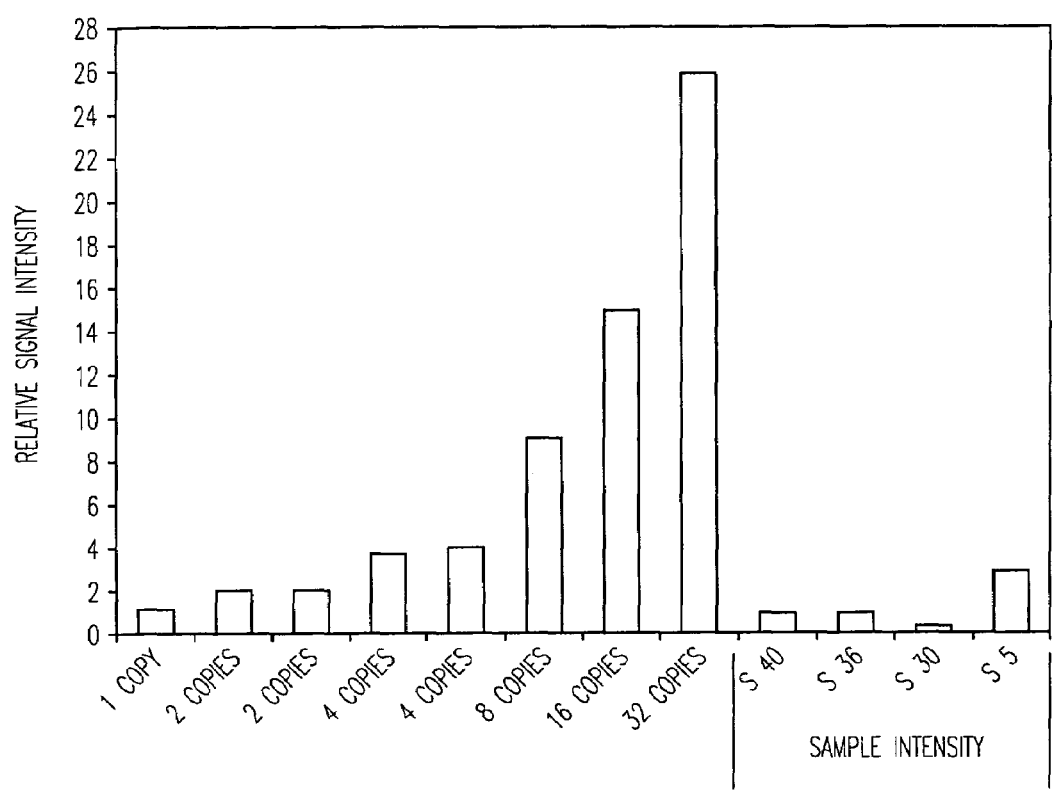
FIG. 14 shows the copy number of integrated pSEAP2-control plasmid in four genetically modified pigs based on densitometric intensities of bands in FIG. 13.

After the pigs were born and grown to 70-day-old pigs, they were analyzed for the presence of the pSEAP2-control plasmid. FIG. 13 shows the southern blot analysis of genomic DNA isolated from the tail tissues of these pigs. Briefly, genomic DNA isolated from these pigs were digested, run on a gel, and transferred to a nylon membrane according to methods well known in the art. The blot was then probed with labeled sequences from the Not I to BamH I region of the pSEAP2-control plasmid shown in FIG. 12. In FIG. 13, M denotes the marker lanes, and 1–43 denotes the number of pigs analyzed. Hybridization signals in lanes 5, 17, 19, 25, 26, 27, 28, 30, 36, 38, 39, and 40 indicated that the pSEAP2-control plasmid had integrated into the corresponding pig's genome. In the lower right half of the figure, eight lanes with increasing copies of pSEAP2-control plasmid molecules (1, 2, 2, 4, 4, 8, 16, and 32) were also loaded on the gel together with the DNA from the experimental pigs. These eight lanes were used to estimate the copy number of pSEAP2-control plasmid integrated into the pigs based on the densitometric intensities of the bands (FIG. 14). As can be seen in FIG. 14, S5 had the highest intensity, which corresponds to lane 5 of FIG. 13.

Figure 15:
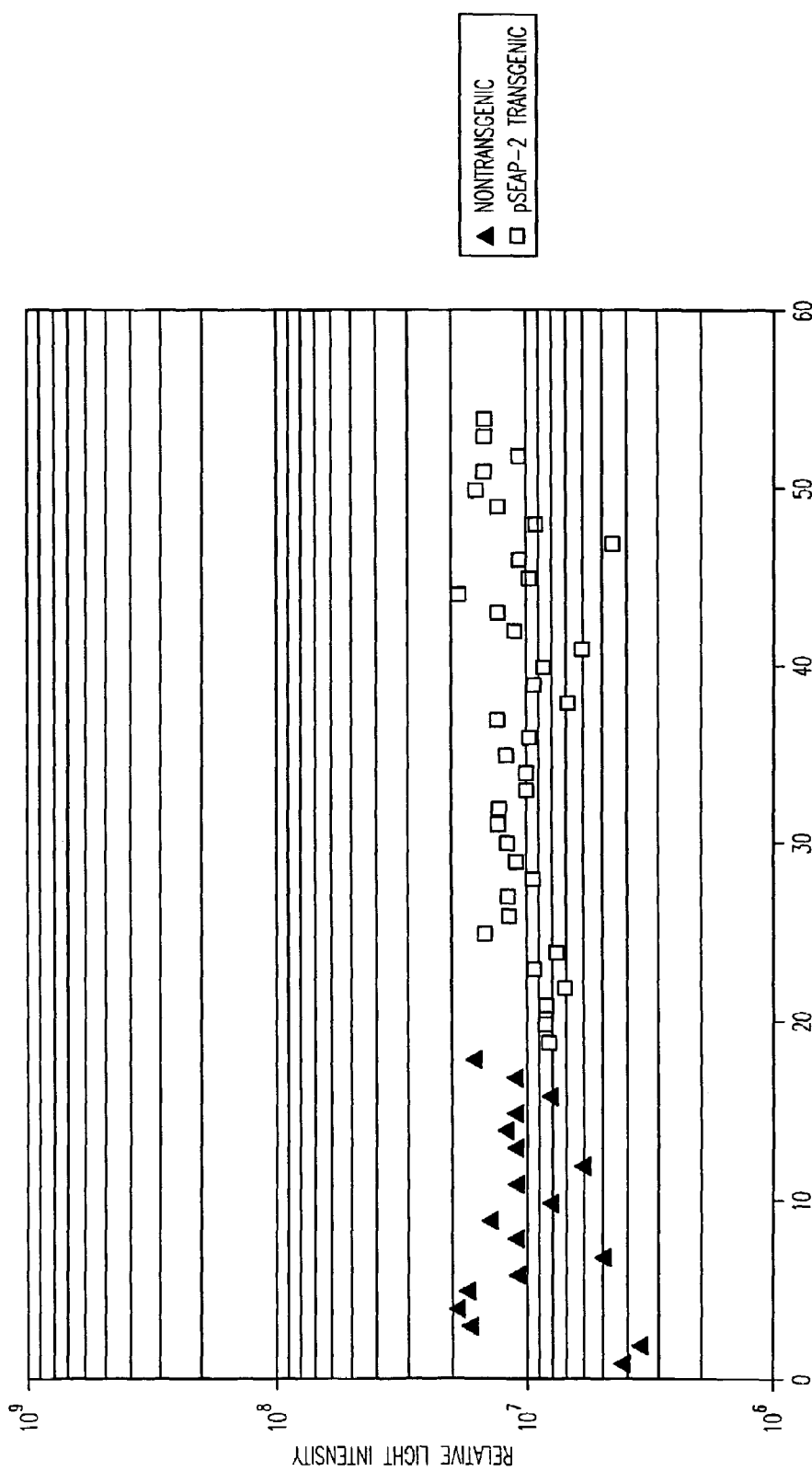
FIGS. 15 and 16 show the results of enzyme assays for secreted alkaline phosphatase found in serum of pigs genetically modified according to one embodiment of the present invention.
Figure 16:
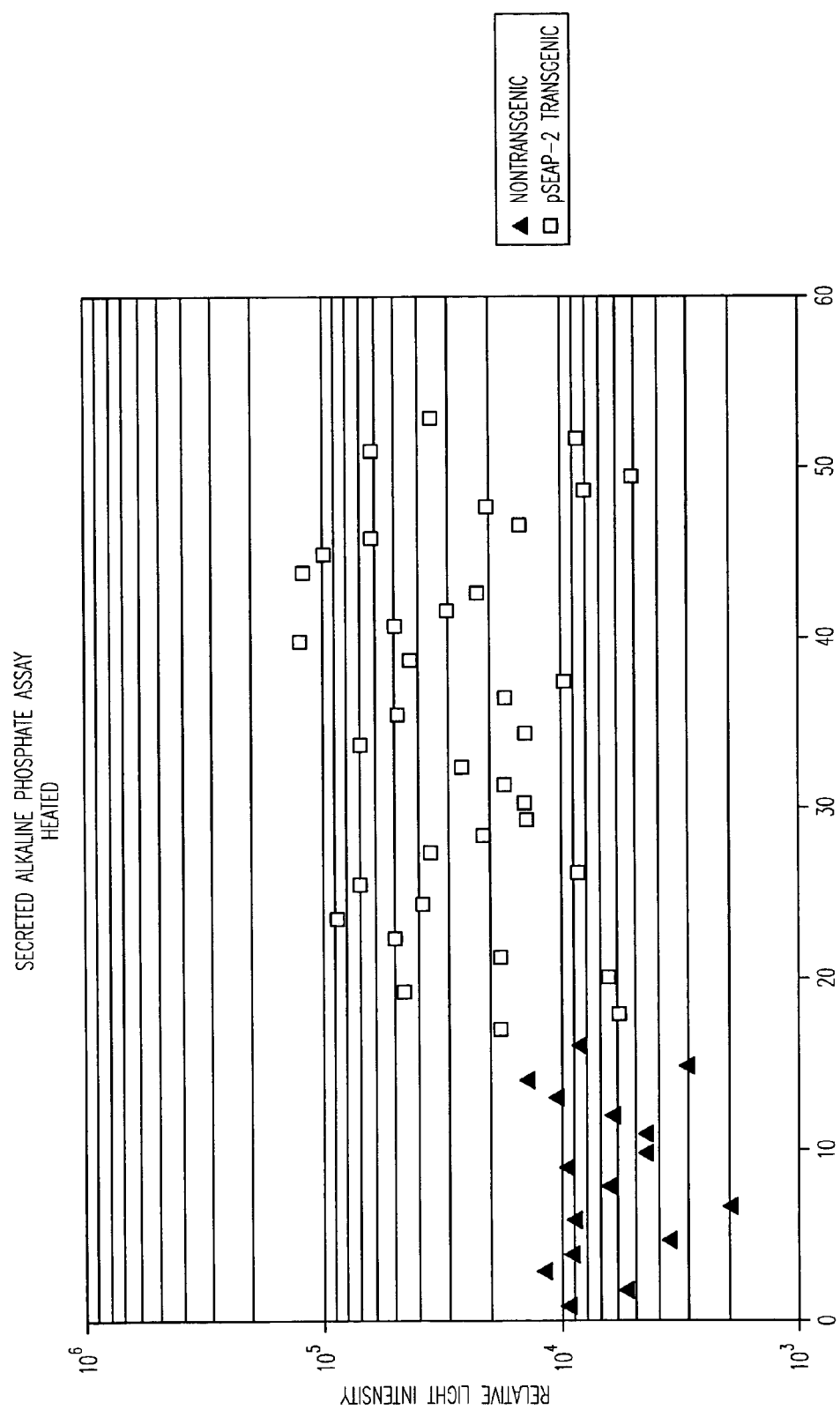

In another study, secreted alkaline phosphatase (SEAP) expressed from the pSEAP2-control plasmid were also detected in 70-day old genetically modified pigs. Serum from these pigs were collected and assayed for SEAP activity using Clontech's Great EscAPE™ SEAP Chemiluminescence Detection Kit (Cat. # K2041-1) and its protocol, which is incorporated herein by reference. The SEAP enzyme expressed from Clontech's pSEAP-2 vector is thermostable. Thus, to determine the level of SEAP activity as opposed to the pigs' endogenous alkaline phosphatase enzyme activity, the assay required the deactivation of the endogenous alkaline phosphatase enzyme by heating the samples at 65° C. for thirty minutes before adding the chemiluminescence substrate. As a control, FIG. 15 shows the result of the assay without performing this heat deactivation step. The level of total alkaline phosphatase activity was not significantly different between the genetically modified pigs and non-transgenic control pigs. In contrast, FIG. 16 shows the result including this heat deactivation step. Without the endogenous alkaline phosphatase activity, SEAP activity was significantly higher in the genetically modified pigs than in the non-transgenic control pigs. Thus, the pSEAP2-control plasmid had integrated well in the pigs' genome and was actively expressing the SEAP enzyme.

The preceding examples demonstrate that the inventor has produced a number of genetically modified animals using the sperm vector as described above. These data are intended only as examples and are not intended to limit the invention to these examples. It is understood that modifying the examples below does not depart from the spirit of the invention.

What is claimed is:

1. A vector comprising:
   a non-human sperm cell; and
   at least one DNA molecule bound to the non-human sperm cell through at least one non-liposome based linker, wherein said linker is the murine monoclonal antibody mAbC secreted by the hybridoma assigned ATCC accession number PTA-6723.

2. The vector of claim 1 wherein the non-liposome based linker is bound to the external surface of the non-human sperm cell.

3. The vector of claim 1 wherein the non-liposome based linker is a sperm-specific linker.

4. The vector of claim 1 wherein the non-liposome based linker binds to the external surface of the non-human sperm cell.

5. The vector of claim 1 wherein the DNA molecule codes for a gene product.

6. The vector of claim 5 wherein the gene product is an RNA molecule.

7. The vector of claim 5 wherein the gene product is a protein.

8. The vector of claim 1 wherein the non-liposome based linker interacts with the at least one DNA molecule via molecular interactions from the group consisting of ionic interaction, covalent interaction, van der Waals interaction, and ligand-receptor interaction.

9. The vector of claim 1 wherein the non-liposome based linker interacts with the at least one DNA molecule through at least one secondary non-liposome based linker.

10. The vector of claim 2 wherein the at least one DNA molecule binds to the external surface of the non-human sperm cell through the non-liposome based linker in vivo.

11. The non-liposome based linker for attaching at least one DNA molecule to the external surface of a non-human sperm's cell, wherein said linker is the murine monoclonal antibody mAbC secreted by the hybridoma assigned ATCC accession number PTA-6723.

12. The non-liposome based linker of claim 11 wherein the linker binds to the external surface of the non-human sperm cell.

13. A composition comprising:
a non-human sperm cell; and
at least one DNA molecule bound to the non-human sperm cell through at least one non-liposome based linker, wherein said linker is the murine monoclonal antibody mAbC secreted by a hybridoma assigned ATCC accession number PTA-6723.

14. The composition of claim 13 wherein the non-liposome based linker is bound to the external surface of the non-human sperm cell.

15. The composition of claim 13 wherein the non-liposome based linker is a sperm-specific linker.

16. The composition of claim 13 wherein the non-liposome based linker binds to the external surface of the non-human sperm cell.

17. The composition of claim 13 wherein the DNA molecule codes for a gene product.

18. The composition of claim 17 wherein the gene product is an RNA molecule.

19. The composition of claim 17 wherein the gene product is a protein.

20. The composition of claim 13 wherein the non-liposome based linker interacts with the at least one DNA molecule via molecular interactions from the group consisting of ionic interaction, covalent interaction, van der Waals interaction, and ligand-receptor interaction.

21. The composition of claim 13 wherein the non-liposome based linker interacts with the at least one DNA molecule through at least one secondary non-liposome based linker.

22. The composition of claim 14 wherein the at least one DNA molecule binds to the external surface of the non-human sperm cell through the non-liposome based linker in vivo.

23. A method of introducing a DNA molecule into a non-human mammalian egg comprising the steps of:
obtaining a non-human mammalian sperm;
associating a DNA molecule to the non-human mammalian sperm cell through at least one non-liposome based linker to form a DNA/non-liposome based linker/non-human mammalian sperm complex, wherein said linker is the murine monoclonal antibody mAbC secreted by the hybridoma assigned ATCC accession number PTA-6723; and
effecting the fertilization of the non-human mammalian egg with the DNA/non-liposome based linker/non-human mammalian sperm complex.

* * * * *